(12) United States Patent
Xi et al.

(10) Patent No.: US 10,123,772 B2
(45) Date of Patent: Nov. 13, 2018

(54) ULTRASONIC DATA ACQUISITION APPARATUS, SYSTEM AND CONTROL METHOD THEREOF

(71) Applicant: Vinno Technology (Suzhou) Co., Ltd., Suzhou, Jiangsu Province (CN)

(72) Inventors: Shui Xi, Suzhou (CN); Yinzhang Bai, Suzhou (CN)

(73) Assignee: VINNO TECHNOLOGY (SUZHOU) CO., LTD., Suzhou, Jiangsu Province (CN)

( * ) Notice: Subject to any disclaimer, the term of this patent is extended or adjusted under 35 U.S.C. 154(b) by 818 days.

(21) Appl. No.: 14/614,359

(22) Filed: Feb. 4, 2015

(65) Prior Publication Data

US 2016/0100820 A1 Apr. 14, 2016

(30) Foreign Application Priority Data

Oct. 13, 2014 (CN) .......................... 2014 1 0537325

(51) Int. Cl.
*A61B 8/00* (2006.01)
*A61B 8/14* (2006.01)

(52) U.S. Cl.
CPC ............ *A61B 8/4461* (2013.01); *A61B 8/145* (2013.01); *A61B 8/4281* (2013.01); *A61B 8/4209* (2013.01); *A61B 8/461* (2013.01); *A61B 8/54* (2013.01)

(58) Field of Classification Search
CPC ..... A61B 8/4281; A61B 8/4461; A61B 8/145; A61B 8/461; A61B 8/4209; A61B 8/54
See application file for complete search history.

(56) References Cited

U.S. PATENT DOCUMENTS

| | | | |
|---|---|---|---|
| 2003/0140044 A1* | 7/2003 | Mok | G06Q 50/22 |
| 2006/0058678 A1* | 3/2006 | Vitek | A61B 8/4281 |
| | | | 600/459 |
| 2007/0276246 A1* | 11/2007 | Lin | A61B 8/00 |
| | | | 600/444 |
| 2009/0171217 A1 | 7/2009 | Kim et al. | |
| 2011/0282212 A1* | 11/2011 | Hyoun | A61B 8/00 |
| | | | 600/459 |

FOREIGN PATENT DOCUMENTS

| | | |
|---|---|---|
| CN | 201642053 U | 11/2010 |
| CN | 103845083 A | 6/2014 |
| CN | 203763102 U | 8/2014 |
| WO | 2004/098413 A1 | 11/2004 |

\* cited by examiner

*Primary Examiner* — Bo J Peng
(74) *Attorney, Agent, or Firm* — Cheng-Ju Chiang

(57) ABSTRACT

An ultrasonic data acquisition apparatus includes an inner layer, a guiding rail surrounding the inner layer and an ultrasonic probe positioned outside of the inner layer and connected to the guiding rail. The inner layer includes an inner surface and an outer surface. The inner layer is curved along a circumference direction. The ultrasonic probe includes a far end adjacent to the tissue and a near end opposite to the far end. When the ultrasonic data acquisition apparatus is in working, the ultrasonic probe is movable relative to the inner layer along the circumference direction while keeping the far end consistently abutting against the outer surface of the inner layer. Besides, a system for acquiring ultrasonic data and a control method of the ultrasonic data acquisition apparatus are also disclosed.

13 Claims, 6 Drawing Sheets

⟨Prior Art⟩

ULTRASONIC DATA ACQUISITION APPARATUS, SYSTEM AND CONTROL METHOD THEREOF

CROSS REFERENCE TO RELATED APPLICATION

The present application claims the priority of Chinese patent application Ser. No. 201410537325.3 filed Oct. 13, 2014 in the SIPO (Sate Intellectual Property Office of the P.R.C.), which is incorporated by reference herein in its entirety.

BACKGROUND

1. Technical Field

The present disclosure relates to an ultrasonic data acquisition apparatus, a system for acquiring ultrasonic data and a control method of the ultrasonic data acquisition apparatus, which belongs to the technical field of medical equipment.

2. Description of Related Art

Medical ultrasound examination is a diagnostic technology based on ultrasonic and imageology, which enables sizes, structures and pathological lesions of the muscles and the internal organs to be visualized.

Ultrasound diagnostics only began in the 20th century and did not have a long history. But, it plays an irreplaceable role in nowadays medical diagnostics. Ultrasound examination has been widely used in medical area. It can be used to diagnose diseases or to play a leading role in the treatment process, i.e., in biopsy or fluid drainage treatment. Usually, a water-based gel is applied to be coupled between a patient's body and a probe, and then the hand-held probe can be used to be placed on the patient's body and move for scanning.

FIG. 1 shows a present ultrasonic data acquisition apparatus which needs to be held by medical personnel and then repeatedly move on the patient's body during scanning. Besides, different parts need different ultrasonic data acquisition apparatus.

Correspondingly, the above ultrasound data acquisition apparatus has following problems. Firstly, since it requires medical personnel to hold the ultrasound data acquisition apparatus by one hand in a long time and constantly move it on the patient's body during scanning, and collect data by the other hand via a keyboard, the pair of hands of the medical personnel cannot alternate. Secondly, when the medical personnel need to scan different parts, it needs to frequently switch the probe, which will increase the workload of the medical personnel, result in cumbersome operation and increase management. Besides, it requires high-level experience and techniques of the medical personnel. Different techniques of the medical personnel may cause different result, which is easy to generate missed diagnosis and misdiagnosis. Furthermore, in the existing mode, both scan and diagnose are done by a single staff, which greatly increases the difficulty of training ultrasound medical staffs.

Hence, it is desirable to provide an improved ultrasonic data acquisition apparatus, an improved system for acquiring ultrasonic data and an improved control method of the ultrasonic data acquisition apparatus.

SUMMARY

The present disclosure provides an ultrasonic data acquisition apparatus including an inner layer, a guiding rail surrounding the inner layer and an ultrasonic probe positioned outside of the inner layer and connected to the guiding rail. The inner layer includes an inner surface and an outer surface. The inner surface is adapted for abutting against a tissue to be detected. The inner layer is curved along a circumference direction. The ultrasonic probe includes a far end adjacent to the tissue and a near end opposite to the far end. When the ultrasonic data acquisition apparatus is in working, the ultrasonic probe is movable relative to the inner layer along the circumference direction while keeping the far end consistently abutting against the outer surface of the inner layer.

The present disclosure also provides a system for acquiring ultrasonic data. The system include the above ultrasonic data acquisition apparatus and a backend server communication with the ultrasonic data acquisition apparatus. The ultrasonic data acquisition apparatus further includes an ultrasonic sending module for sending ultrasonic signals, an ultrasonic receiving module for receiving the ultrasonic signals, a wave beam synthetic module for synthesizing the received ultrasonic signals into data, a data storage module for storing the data, a data transmission module for transmitting the data to the backend server, and a power module for supplying power to the ultrasonic data acquisition apparatus. The backend server includes a data module for receiving and analyzing the data transmitted from the data transmission module, and a display for displaying an analysis result.

The present disclosure further discloses a control method of an ultrasonic data acquisition apparatus. The control method includes steps of: S1: installing the ultrasonic data acquisition apparatus to a tissue with the inner surface abutting against the tissue; S2: filling air or liquid into the capsule under the detection of the pressure detecting part; S3: stopping filling and sealing the capsule when the pressure detecting part detects the inner layer has fully attached the tissue; and S4: the ultrasonic probe is movable relative to the inner layer along the circumference direction while keeping the far end consistently abutting against the outer surface of the inner layer.

The foregoing has outlined rather broadly the features and technical advantages of the present disclosure in order that the detailed description of the invention that follows may be better understood. Additional features and advantages of the invention will be described hereinafter which form the subject of the claims of the invention.

BRIEF DESCRIPTION OF THE DRAWINGS

The components in the drawing are not necessarily drawn to scale, the emphasis instead being placed upon clearly illustrating the principles of the described embodiments. In the drawings, reference numerals designate corresponding parts throughout various views, and all the views are schematic.

DETAILED DESCRIPTION OF ILLUSTRATED EMBODIMENTS

Figure 1:
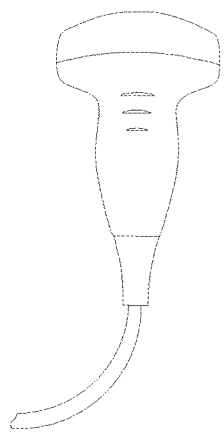
FIG. 1 shows a prior art ultrasonic data acquisition apparatus.

Reference will now be made to the drawing figures to describe the embodiments of the present disclosure in detail. In the following description, the same drawing reference numerals are used for the same elements in different drawings.

Referring to FIGS. 2A to 2D, the present disclosure discloses an ultrasonic data acquisition apparatus for moveably scanning a tissue to be detected. The tissue is usually a human body, i.e., the neck, chest or abdomen of a patient. Since the working principle of the present disclosure is understandable to those of ordinary skill in the art, detailed description thereof is omitted herein.

For better depiction and understanding, words used to describe positions and directions in the present disclosure refer to an operator. For example, one end of the ultrasonic data acquisition apparatus adjacent to the operator is defined as a near end, and the other end far from the operator is defined as a far end.

Referring to FIGS. 2A to 2D, the ultrasonic data acquisition apparatus includes an inner layer 10, a guiding rail 50 surrounding the inner layer 10, an ultrasonic probe 30 associated with the guiding rail 50 and an outer layer 70 for protecting the ultrasonic probe 30.

The inner layer 10 includes an inner surface 101 and an outer surface 102 opposite to the inner surface 101. The inner surface 101 is adapted for abutting against a tissue (not shown) to be detected. The inner layer 10 is curved along a circumference direction. According to the first illustrated embodiment of the present disclosure, the inner layer 10 is of an annular configuration and is deformable for matching size of the tissue.

The ultrasonic probe 30 is positioned outside of the inner layer 10 and connected to the guiding rail 50. The ultrasonic probe 30 includes a far end 301 adjacent to the tissue and a near end 302 opposite to the far end 301. The far end 301 includes a first protrusion 303 defining a first recess 304 and a second protrusion 305 defining a second recess 306.

Figure 2A:
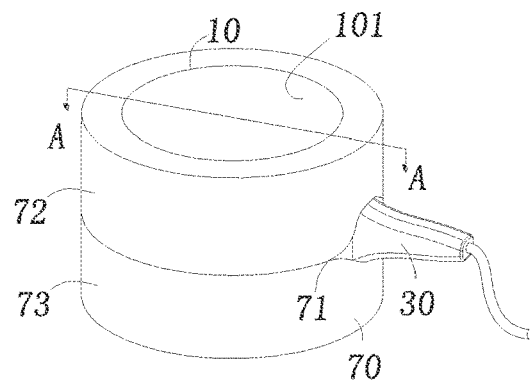
FIG. 2A is a schematic perspective view of an ultrasonic data acquisition apparatus in accordance with a first embodiment of the present disclosure.
Figure 2B:
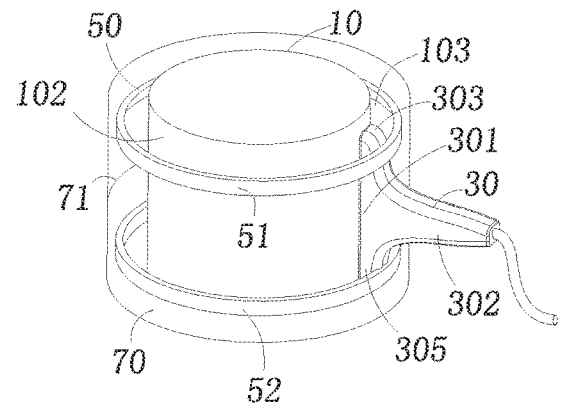
FIG. 2B is a transparent perspective view of FIG. 2A.
Figure 2C:
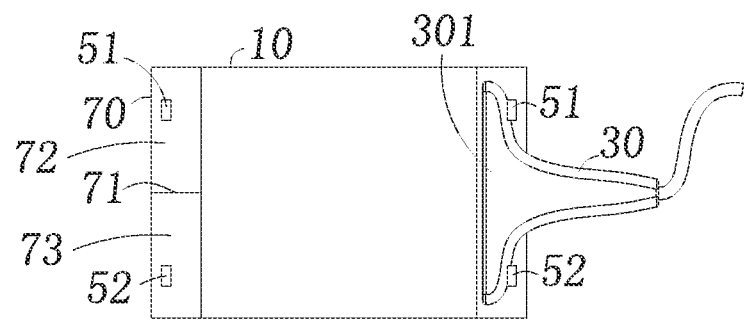
FIG. 2C is a cross sectional view taken along A-A of FIG. 2A.
Figure 2D:
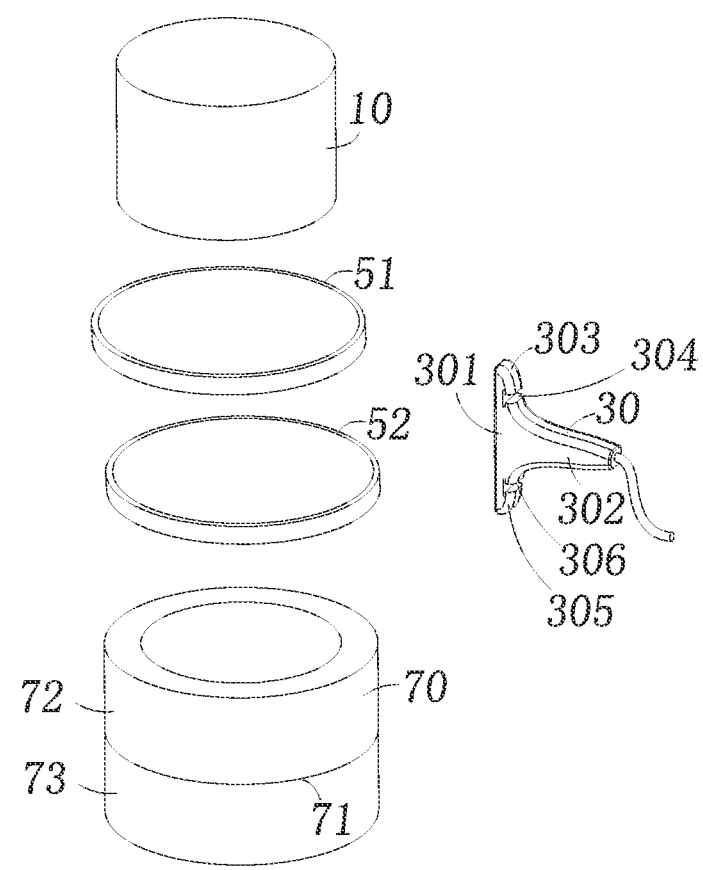
FIG. 2D is an exploded view of FIG. 2A.

Referring to FIG. 2B, the guiding rail 50 and the ultrasonic probe 30 are installed between the inner layer 10 and the outer layer 70. The inner layer 10 and the guiding rail 50 form an annular gap 103 therebetween. The far end 301 of the ultrasonic probe 30 is slidably received in the annular gap 103. According to the first illustrated embodiment of the present disclosure, the guiding rail 50 includes a first guiding rail 51 and a second guiding rail 52 separated a distance from the first guiding rail 51 along an axis direction. After assembly, the first protrusion 303 and the second protrusion 305 are outwardly restricted by the first guiding rail 51 and the second guiding rail 52, respectively. Besides, The first guiding rail 51 and the second guiding rail 52 are received in the first recess 304 and the second recess 306, respectively.

When the ultrasonic data acquisition apparatus is in working, the ultrasonic probe 30 is movable relative to the inner layer 10 along the circumference direction while keeping the far end 301 consistently abutting against the outer surface 102 of the inner layer 10. The inner layer 10 provides a scanning surface for the ultrasonic probe 30 for collecting information.

The outer layer 70 is elastic and defines a faying slit 71 along which the near end 302 is movable when the ultrasonic data acquisition apparatus is in working. A part of the faying slit 71 is enlarged so as to expose the near end 302 to an exterior while a remaining part of the faying slit 71 keeps closed. As a result, the ultrasonic probe 30 can be prevented from being contaminated by outer substance. Besides, since the outer layer 70 is elastic, it can also play a role of positioning the ultrasonic probe 30 in order to keep the far end 301 consistently abutting against the outer surface 102 of the inner layer 10. The outer layer 70 includes an upper portion 72 and a lower portion 73 with the faying slit 71 formed therebetween. The faying slit 71 extends along the circumference direction.

According to the first illustrated embodiment of the present disclosure, the inner layer 10 is of an integral configuration and is deformable itself. In using, when the ultrasonic data acquisition apparatus surrounds the tissue, the size of the ultrasonic data acquisition apparatus can be automatically adjusted to adapt the tissue so that the inner layer 10 can keep contacting the tissue.

The inner layer 10 can be made of silicone rubber based composite polymer materials so that the molecular structure of the inner layer 10 can be similar to the tissue. Under this condition, the ultrasonic probe 30 can be maximum coupling with the tissue to be detected in order to get an accurate test result.

According to the illustrated embodiments of the present disclosure, the first recess 304 and the second recess 306 are symmetrically formed on the far end 301 along a horizontal direction perpendicular to the axis direction. As a result, the ultrasonic probe 30 can be kept to abut against the outer surface 102 of the inner layer 10 more stably, when the ultrasonic data acquisition apparatus is in working. Understandably, in alternative embodiments, the recess 304 and/or the recess 306 can be set on the guiding rail 50, and the ultrasonic probe 30 can form a protuberance to mate with the recess. Under this condition, the ultrasonic probe 30 can also be movable along a predetermined track relative to the guiding rail 50. The size and length of the guiding rail 50 has no specific restriction, and they are defined in accordance with the movable track of the ultrasonic probe 30.

In one embodiment, the guiding rail 50 is immovable with respect to the inner layer 10 and the ultrasonic probe 30 is slidably or movably connected to the guiding rail 50. Of course, in alternative embodiments, the guiding rail 50 can be set immovable with respect to the outer layer 70 of which detailed description is omitted herein.

In another embodiment, the ultrasonic probe 30 is fixed to the guiding rail 50. The guiding rail 50 includes an inner portion a part of which abuts against the inner layer 10 and an outer portion a part of which abuts against the outer layer 70. When the ultrasonic data acquisition apparatus is in working, the ultrasonic probe 30 is driven by the guiding rail 50 to be movable relative to the inner layer 10.

In another embodiment, the ultrasonic probe 30 is movably connected to the guiding rail 50. The guiding rail 50 includes an inner portion a part of which abuts against the inner layer 10 and an outer portion a part of which abuts against the outer layer 70. When the ultrasonic data acquisition apparatus is in working, the guiding rail 50 is movable relative to the inner layer 10 and the ultrasonic probe 30 is movable relative to the guiding rail 50.

Figure 3A:
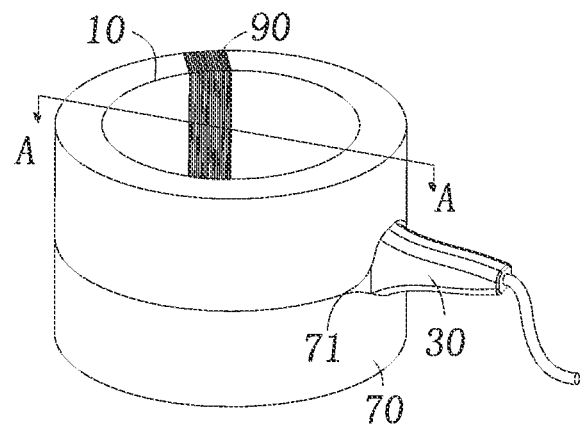
FIG. 3A is a schematic perspective view of an ultrasonic data acquisition apparatus in accordance with a second embodiment of the present disclosure.
Figure 3B:
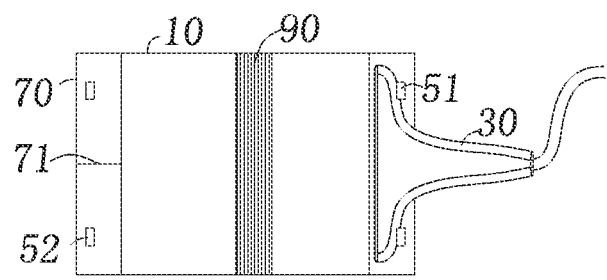
FIG. 3B is a cross sectional view taken along A-A of FIG. 3A.
Figure 3C:
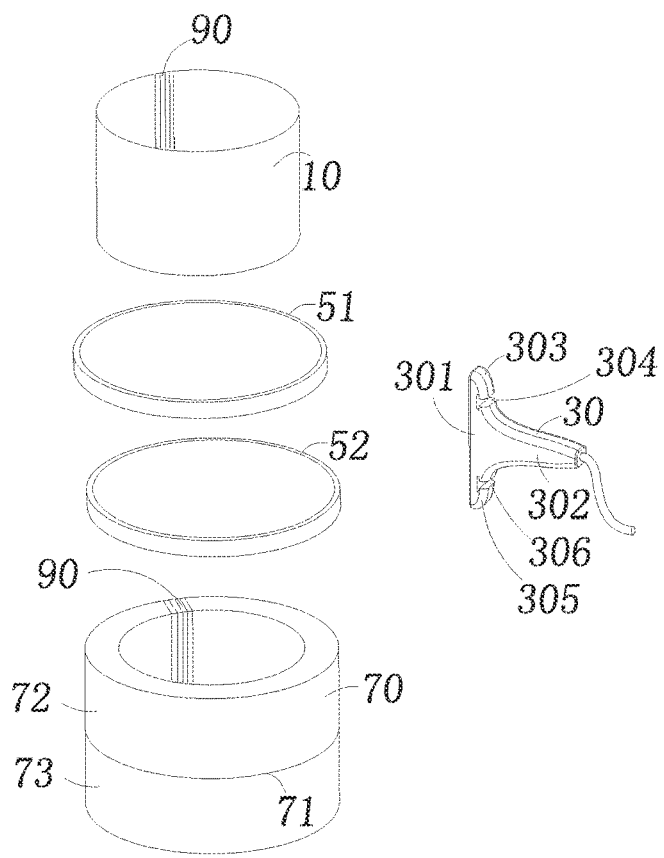
FIG. 3C is an exploded view of FIG. 3A.

Referring to FIGS. 3A to 3C, a second embodiment of the present disclosure discloses an ultrasonic data acquisition apparatus which is very similar to that in the first embodiment. The ultrasonic data acquisition apparatus in the second embodiment includes a C-shaped the inner layer 10 and an adjustment portion 90 interconnecting the inner layer 10. The adjustment portion 90 fills in a gap of the C-shaped the inner layer 10. The adjustment portion 90 can be used to adjust the size of the ultrasonic data acquisition apparatus for adapting different tissues. Understandably, a cross section of the outer layer 70 can also be a C-shaped configuration, and the adjustment portion 90 can fill in a gap of the C-shaped the outer layer 70 at the same time.

The adjustment portion 90 is elastic, such as a spring or an elastic cord, in order that the inner layer 10 can be deformable for matching sizes of different tissues.

Besides, the adjustment portion 90 can also be a lock, such as a buckle, or a case lock, or a watch lock, or a sticking lock etc. As a result, the inner layer 10 can be deformable to match sizes of different tissues. Detailed description about the adjustment portion 90 is omitted herein.

Figure 4:
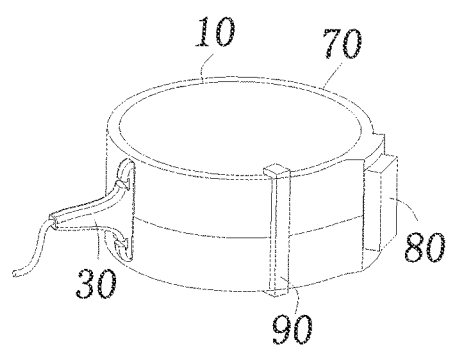
FIG. 4 is a schematic perspective view of an ultrasonic data acquisition apparatus in accordance with a third embodiment of the present disclosure.

Referring to FIG. 4, in order to match with the tissue to be detected, the ultrasonic data acquisition apparatus further includes a pressure attachment unit 80 mounted outside of the inner layer 10 in order to adjust size of the ultrasonic data acquisition apparatus. The pressure attachment unit 80 includes a capsule (not shown) for filling air or liquid and a pressure detecting part (not shown) for detecting filling status of the capsule. The pressure attachment unit 80 is attached to the outer surface 102 of the inner layer 10. When in the air or liquid is filled into the capsule, it will squeeze the inner layer 10 to make the inner layer 10 in close contact with the tissue.

Referring to FIG. 4, in the illustrated embodiment, the adjustment portion 90 is a lock which cooperates with the pressure attachment unit 80 to adjust the size of the ultrasonic data acquisition apparatus. Detailed description thereof will be given hereinafter. It is understandable to those of ordinary skill in the art that structures of the inner layers 10 can be set in different configurations in accordance with different tissues. For example, if the tissue to be detected is a human head, the inner layer 10 can be designed like a helmet. If the tissue to be detected is a human food, the inner layer 10 can be designed like a shoe. Besides, the inner layer 10 can also be designed like a cloth to be directly worn by a patient. Accordingly, the inner layer 10, such as the helmet and the cloth, can be integrally formed. Unlike the conventional ultrasonic data acquisition apparatus which has multiple ultrasonic probes, the ultrasonic data acquisition apparatus according to the present disclosure will greatly decrease the workload of medical staffs.

Besides, in another embodiment of the present disclosure, the ultrasonic data acquisition apparatus further includes a drive motor (not shown) to drive the ultrasonic probe 30 automatically moving relative to the inner layer 10 when the ultrasonic data acquisition apparatus is in working. As a result, the scanning procedure can be standardized, which avoids different scanning result by different techniques of the medical personnel. According to the present disclosure, since a non-professional person can use this apparatus as well, it is possible for such ultrasonic data acquisition apparatus to access family usage.

Furthermore, due to the standardized scanning procedure, it is needless for the medical personnel to deal with the scanning result in real. It is possible to add a computer-aided diagnosis function in the ultrasonic data acquisition apparatus. Under this condition, the ultrasonic data acquisition apparatus can only be provided with limited functions, i.e., sending and receiving ultrasonic, storing and transmitting data. This ultrasonic data acquisition apparatus can be apart from the functions of ultrasonic after treatment and display. Alternatively, the data acquired by the ultrasonic data acquisition apparatus can be sent to a backend server via networks for image , and then the data can be processed by the computer-aided diagnosis, analysis and display. As a result, it is possible to apart the scanning from the diagnosing and make the ultrasonic data acquisition apparatus suitable for family use.

Figure 5:
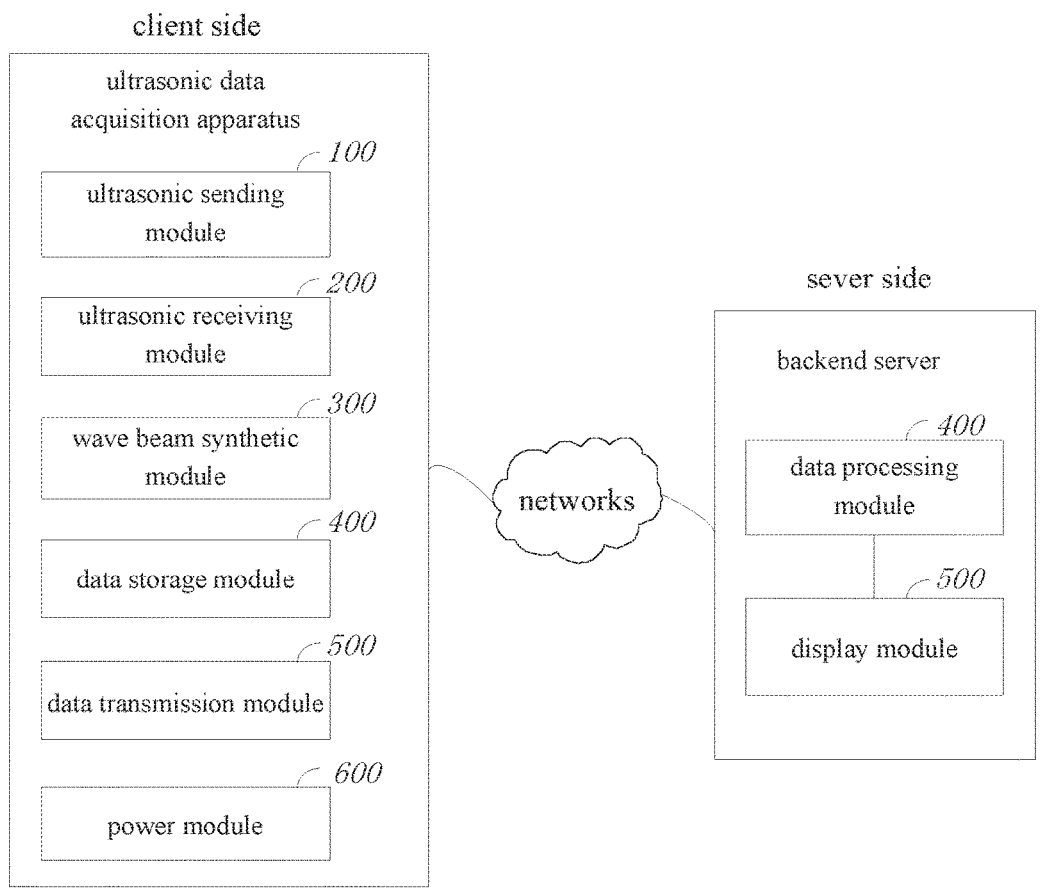
FIG. 5 is a schematic view of a system showing the ultrasonic data acquisition apparatus in FIG. 2A connected to a backend server via networks.

Referring to FIG. 5, a system for acquiring ultrasonic data is disclosed. The system includes an ultrasonic data acquisition apparatus and a backend server communication with the ultrasonic data acquisition apparatus through networks. The ultrasonic data acquisition apparatus is set in a client side. The networks include internet, Bluetooth, local area networks or wide area networks etc. As a result, the data acquired and stored by the ultrasonic data acquisition apparatus can be sent to the backend server for . The backend sever includes a personal computer, a cloud platform, or a mobile device etc.

Besides, the ultrasonic data acquisition apparatus further included an ultrasonic sending module 100 for sending ultrasonic signals, an ultrasonic receiving module 200 for receiving the ultrasonic signals, a wave beam synthetic module 300 for synthesizing the received ultrasonic signals into data, a data storage module 400 for storing the data, a data transmission module 500 for transmitting the data to the backend server and a power module 600 for supplying power to the ultrasonic data acquisition apparatus.

The backend server includes a data processing module 700 for receiving and analyzing the data transmitted from the data transmission module 500, and a display 800 for displaying an analysis result.

Figure 6:
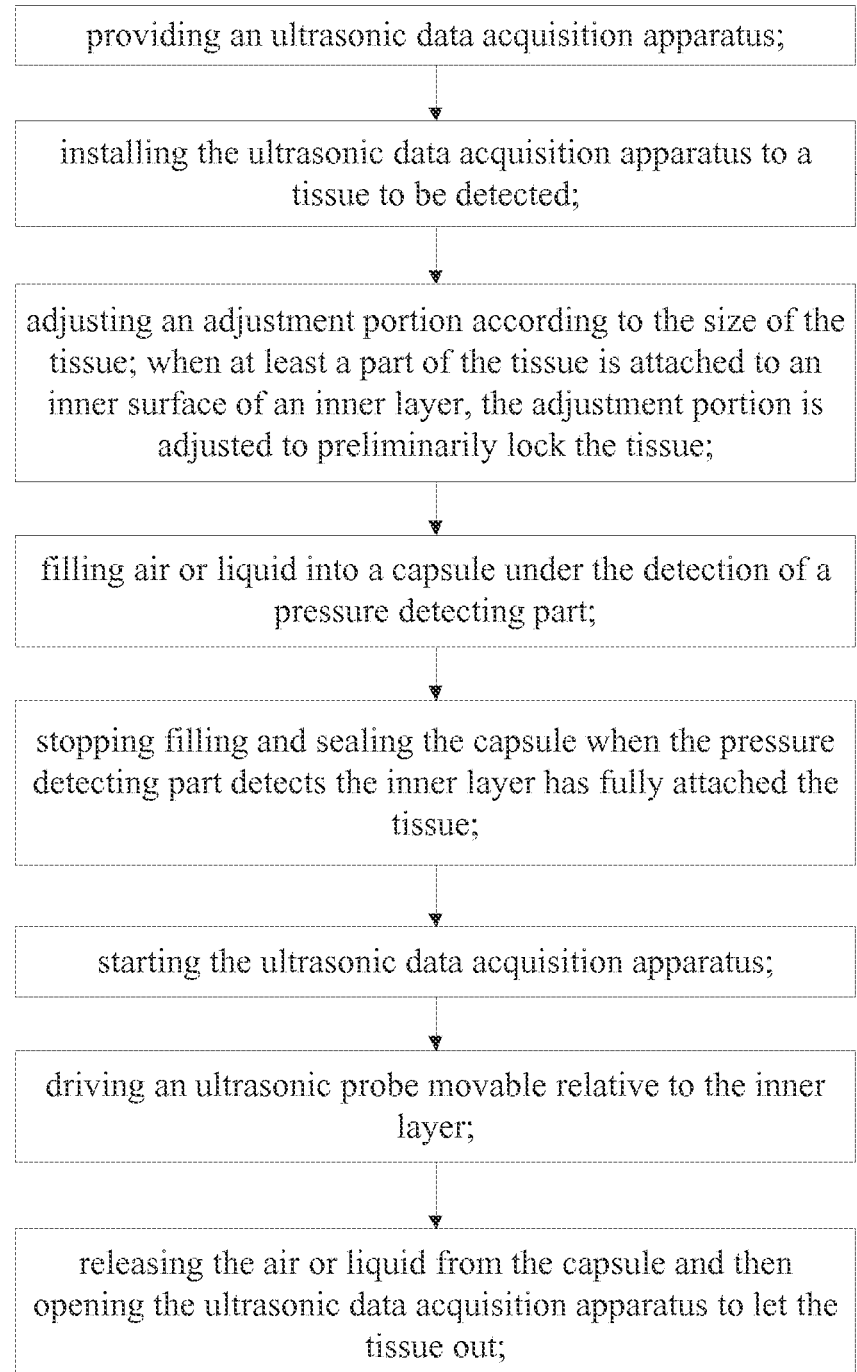
FIG. 6 a schematic view showing a control method of the ultrasonic data acquisition apparatus in FIG. 2A.

The present disclosure also discloses a control method of the ultrasonic data acquisition apparatus as shown in FIG. 6. The control method includes the steps of:

S1: installing the ultrasonic data acquisition apparatus to a tissue with the inner surface 101 abutting against the tissue;

S2: filling air or liquid into the capsule under the detection of the pressure detecting part;

S3: stopping filling and sealing the capsule when the pressure detecting part detects the inner layer 10 has fully attached the tissue;

S4: the ultrasonic probe 30 is movable relative to the inner layer 10 along the circumference direction while keeping the far end 301 consistently abutting against the outer surface 102 of the inner layer 10;

S5: releasing the air or liquid from the capsule and then opening the ultrasonic data acquisition apparatus to let the tissue out.

In the step S1, take a abdomen as the tissue for example, firstly, opening the adjustment portion 90 and letting the pressure attachment unit 80 unfilled so as to easily enclose the ultrasonic data acquisition apparatus on the abdomen. Take the adjustment portion 90 as a lock for example. When at least a part of the abdomen is attached to the inner surface 101 of the inner layer 10, the lock is adjusted to preliminarily lock the abdomen. The lock can be set a lot of tap positions for different size adjustment. Of course, the preliminary lock can be omitted, which means that when the tissue is enclosed in position, the ultrasonic data acquisition apparatus can be directly adjusted by the pressure attachment unit 80.

After such scanning, the acquired data will be sent to the backend server for . Please refer to the detailed description above.

It is to be understood, however, that even though numerous characteristics and advantages of preferred and exemplary embodiments have been set out in the foregoing description, together with details of the structures and functions of the embodiments, the disclosure is illustrative only; and that changes may be made in detail within the principles of present disclosure to the full extent indicated by the broadest general meaning of the terms in which the appended claims are expressed.

What is claimed is:

1. An ultrasonic data acquisition apparatus comprising:
    an inner layer comprising an inner surface and an outer surface, the inner surface being adapted for abutting against a tissue to be detected, the inner layer being curved along a circumference direction;
    a guiding rail surrounding the inner layer; and
    an ultrasonic probe positioned outside of the inner layer and connected to the guiding rail, the ultrasonic probe comprising a far end adjacent to the tissue and a near end opposite to the far end;
    an outer layer covering the inner layer to protect the ultrasonic probe, the guiding rail and the ultrasonic probe being installed between the inner layer and the outer layer; wherein
    when the ultrasonic data acquisition apparatus is in working, the ultrasonic probe is movable relative to the inner layer along the circumference direction while keeping the far end consistently abutting against the outer surface of the inner layer; and
    wherein the outer layer is elastic and defines a faying slit along which the near end is movable when the ultrasonic data acquisition apparatus is in working, a part of the faying slit being enlarged so as to expose the near end to an exterior while a remaining part of the faying slit keeps closed.

2. The ultrasonic data acquisition apparatus as claimed in claim 1, wherein the outer layer comprises an upper portion and a lower portion with the faying slit formed therebetween, the faying slit extending along the circumference direction.

3. The ultrasonic data acquisition apparatus as claimed in claim 1, wherein the inner layer and the guiding rail form an annular gap therebetween, and the far end of the ultrasonic probe is slidably received in the annular gap.

4. The ultrasonic data acquisition apparatus as claimed in claim 3, wherein the guiding rail comprises a first guiding rail and a second guiding rail separated a distance from the first guiding rail, the far end comprising a first protrusion outwardly restricted by the first guiding rail and a second protrusion outwardly restricted by the second guiding rail, the near end extending outwardly between the first guiding rail and the second guiding rail.

5. The ultrasonic data acquisition apparatus as claimed in claim 4, wherein the first protrusion defines a first recess to receive the first guiding rail and the second protrusion defines a second recess to receive the second guiding rail.

6. The ultrasonic data acquisition apparatus as claimed in claim 1, wherein the inner layer is of an annular configuration and the inner layer is deformable for matching size of the tissue.

7. The ultrasonic data acquisition apparatus as claimed in claim 1, wherein the inner layer is of a C-shaped configuration, the ultrasonic data acquisition apparatus further comprises an adjustment portion to interconnect the inner layer, the adjustment portion is a spring, or an elastic cord, or a lock in order that the inner layer is deformable for matching size of the tissue.

8. The ultrasonic data acquisition apparatus as claimed in claim 1, further comprising a pressure attachment unit mounted outside of the inner layer in order to adjust size of the ultrasonic data acquisition apparatus.

9. The ultrasonic data acquisition apparatus as claimed in claim 8, wherein the pressure attachment unit comprises a capsule for filling air or liquid and a pressure detecting part for detecting filling status of the capsule.

10. The ultrasonic data acquisition apparatus as claimed in claim 1, wherein the guiding rail is fixed to the inner layer or the outer layer; the ultrasonic probe is movably connected to the guiding rail; when the ultrasonic data acquisition apparatus is in working, the ultrasonic probe is movable relative to the guiding rail; the near end of the ultrasonic probe defines a recess in which the guiding rail is received.

11. The ultrasonic data acquisition apparatus as claimed in claim 1, wherein the ultrasonic probe is fixed to the guiding rail, the guiding rail comprises an inner portion a part of which abuts against the inner layer and an outer portion a part of which abuts against the outer layer; when the ultrasonic data acquisition apparatus is in working, the ultrasonic probe is driven by the guiding rail to be movable relative to the inner layer; the near end of the ultrasonic probe defines a recess in which the guiding rail is received.

12. The ultrasonic data acquisition apparatus as claimed in claim 1, wherein the ultrasonic probe is movably connected to the guiding rail, the guiding rail comprises an inner portion a part of which abuts against the inner layer and an outer portion a part of which abuts against the outer layer; when the ultrasonic data acquisition apparatus is in working, the guiding rail is movable relative to the inner layer and the ultrasonic probe is movable relative to the guiding rail; the near end of the ultrasonic probe defines a recess in which the guiding rail is received.

13. The ultrasonic data acquisition apparatus as claimed in claim 1, further comprising a drive motor to drive the ultrasonic probe automatically moving relative to the inner layer when the ultrasonic data acquisition apparatus is in working.

* * * * *